United States Patent [19]

McCulloch et al.

[11] Patent Number: 5,177,299
[45] Date of Patent: Jan. 5, 1993

[54] RECOVERY OF HIGH OCTANE COMPONENTS FROM ISOMERATES

[75] Inventors: Beth McCulloch, Clarendon Hills; James R. Lansbarkis, Wood Dale; Hemant P. Agrawal, Evanston, all of Ill.

[73] Assignee: UOP, Des Plaines, Ill.

[21] Appl. No.: 814,537

[22] Filed: Dec. 30, 1991

[51] Int. Cl.⁵ .......................... C07C 7/12; C07C 7/00
[52] U.S. Cl. .................................... 585/826; 585/820; 585/853
[58] Field of Search ........................ 585/820, 826, 853

[56] References Cited

U.S. PATENT DOCUMENTS

| | | | |
|---|---|---|---|
| 2,935,539 | 5/1960 | Gladrow et al. | 260/676 |
| 2,956,089 | 10/1960 | Mattox et al. | 260/676 |
| 2,966,528 | 12/1960 | Haensel | 260/666 |
| 2,985,589 | 5/1961 | Broughton et al. | 210/34 |
| 3,442,794 | 5/1969 | Van Helden et al. | 208/111 |
| 3,706,813 | 12/1972 | Neuzil | 260/676 |
| 3,755,144 | 8/1973 | Asselin | 208/95 |
| 3,825,490 | 7/1974 | Vachuda | 585/826 |
| 3,836,597 | 9/1974 | Sie | 260/683.65 |
| 4,717,784 | 1/1988 | Stem et al. | 585/738 |
| 4,855,529 | 8/1989 | Stem et al. | 585/737 |
| 4,982,052 | 1/1991 | Nolte | 585/826 |

Primary Examiner—Anthony McFarlane
Assistant Examiner—Nhat Phan
Attorney, Agent, or Firm—Thomas K. McBride; John F. Spears, Jr.; Jack H. Hall

[57] ABSTRACT

An adsorption process for separating the high octane components, including multi-branched paraffins and isopentane of a $C_5$-$C_6$ isomerate from lower octane monobranched and normal paraffin components by contacting the isomerate with an X zeolite exchanged with a mixture of at least two cations from Group II-A. The adsorbed low octane components are preferably desorbed with a desorbent selected from the group consisting essentially of isooctane, 2,2,3-trimethyl pentane, 2,2,4-trimethyl pentane, 2,3,4-trimethyl pentane, 1,2-dimethyl cyclohexane, 2,2-dimethyl hexane, 2,2-dimethyl octane, 3-ethyl hexane, 2,2,4-trimethyl hexane and mixtures thereof.

12 Claims, 3 Drawing Sheets

RECOVERY OF HIGH OCTANE COMPONENTS FROM ISOMERATES

FIELD OF THE INVENTION

The invention relates to the production of high octane fuels including associated fields of isomerization of naphtha streams and adsorptive separation of an isomerate into its higher octane components, to be used for enhancing the gasoline pool, and its lower octane components, which can be recycled to the isomerization reaction step to increase the yield of the higher octane components.

BACKGROUND OF THE INVENTION

Light straight run naphtha, virgin naphtha and other refinery streams containing $C_5$ and $C_6$ paraffins, are useful sources of blending stock for gasoline pools, but, under current market conditions and ecological considerations, it is necessary to raise the Research Octane Number (RON) of the stock to about 85 to 90 (RON), without the addition of alkyl lead compounds. Since the phase-out of lead compounds began, refiners have relied on isomerization and reforming, e.g., platforming, steps to increase the octane to above about 80 RON and further, have integrated separation processes to separate the isomerate or reformate into higher and lower octane fractions, with the higher octane fraction typically about 90 RON, being sent to the gasoline pool. The lower octane fraction(s) may be recycled to the isomerization step for further conversion and higher yields of multi-branched, high octane paraffins.

In one approach to the upgrading of isomerate streams, U.S. Pat. Nos. 4,717,784 and 4,855,529 disclose similar processes for isomerizing a hydrocarbon feed and separating the dimethyl branched paraffins produced in the reaction from the n-paraffins and monomethyl branched paraffins produced by utilizing a size- or shape-selective adsorbent. In the adsorptive separation step, the straight chain and singly branched paraffins are adsorbed into the pores of the molecular sieve while the more highly branched paraffins are excluded from entering the pores. The selectively adsorbed straight chain paraffins and/or the singly branched paraffins are recycled to the isomerization zone for further conversion to more highly branched paraffins. In this separation, the useful adsorbents have pore sizes in the range from $4.5 \times 4.5$ Å to $5.5 \times 5.5$ Å which exclude the di-branched paraffins from the pores of the molecular sieve. The preferred desorbent in the processes is hydrogen. The patentees teach that only sieves within this range are operative and others having pore sizes outside the range are too small or too large to perform the separation.

U.S. Pat. No. 2,956,089 discloses a process for separating di-branched and cyclic hydrocarbons from singly-branched hydrocarbons using 13A zeolitic molecular sieves. The single-branched hydrocarbons are selectively adsorbed and recovered by desorption. The disclosed feed did not contain isopentane.

U.S. Pat. No. 2,935,539 discloses a process for extracting di-branched paraffins from less highly branched chain paraffins with metallic amine complex-exchanged aluminosilicate zeolites. Desorption may be effected by, e.g., heating the adsorbent or displacement by a hydrocarbon boiling higher or lower than the extract material.

Neuzil U.S. Pat. No. 3,706,813 discloses the separation of dimethyl butanes from methyl pentanes and normal hexanes by selectively adsorbing the multi-branched components on barium- or barium and potassium-exchanged X or Y zeolites containing from 1-10% (wt.) water. Neuzil additionally discloses that the selectivity of the above adsorbents is reversed when the adsorbent is dry, presumably below about 1% (LOI), namely, that the normal and singly-branched paraffins are selectively adsorbed. Neuzil disclosed light desorbents, e.g., isobutane and isopentane, although other multi-branched, singly-branched, normal or cyclic paraffins having at least one carbon number less or greater than the feed components were stated to be useful.

Isomerization processes for converting normal paraffins to mono- and di- or more highly branched chain paraffins are commonly used as a method for increasing the octane rating of refinery streams containing normal paraffins. Illustrative of the isomerization process are U.S. Pat. Nos. 3,755,144 to Asselin and 2,966,528 to Haensel.

U.S. Pat. No. 3,755,144 also discloses the separation of normal paraffins from the isomerization reactor effluent using a molecular sieve in a simulated moving bed system and recycling the normal paraffins to the isomerization reactor after recovering the desorbent. Isohexane is recovered from the extract in a deisohexanizer column and recycled to the isomerization reactor; isopentane and dimethyl butane are taken overhead while cyclic paraffins are recovered in the bottoms of the deisohexanizer. U.S. Pat. No. 2,966,528 further discloses a swing bed system operating under liquid phase conditions for the separation of normal hydrocarbons from branched hydrocarbons in which the normal hydrocarbons are selectively adsorbed and desorbed from the adsorbent with a normal paraffin desorbent.

Accordingly, it is an object of the invention to provide a process for continuously separating di-branched paraffins from normal paraffins and mono-branched paraffins produced by an isomerization reaction with a particular adsorbent/desorbent combination by which the mono-branched, cyclic and normal paraffins having lower octane numbers are selectively adsorbed onto the desorbent. High octane components, di-branched paraffins and isopentane, are relatively selectively non-adsorbed by the adsorbent and are recovered from the non-selective void volume as raffinate. Through the use of an X zeolite molecular sieve having at least two cations from Group IIA metals at the exchange sites, applicants achieve excellent separation of multi-branched paraffins from lower octane mono-branched paraffins and normal paraffins. In addition, isopentane, a mono-branched paraffin which has a high octane rating, i.e., about 92, is also selectively non-adsorbed and separate recovery of isopentane for enhancing the octane rating of gasoline blends is avoided. The lower octane mono-branched paraffins (other than isopentane), cyclic paraffins and normal paraffins are desorbed from the selective pore volume by a carefully selected desorbent and recycled to the isomerization step for further upgrading. The desorbent is a branched or cyclic paraffin having a boiling point different from the feed composition.

SUMMARY OF THE INVENTION

This invention provides a method for separating an isomerization feed stream into a fraction having components high in octane value and a fraction lower in octane value. The high octane components include the highly branched paraffins, e.g., dimethyl paraffins, and isopentane. These components of an isomerate feed stream are valuable since the addition thereof to the gasoline pool will increase the overall octane value of the pool. The low octane fraction, containing monomethyl paraffins (other than isopentane), cyclic paraffins and normal paraffins, can be recycled to the isomerization process and combined with fresh feed for conversion to additional highly branched paraffins.

The method of separation comprises contacting the isomerate stream at adsorption conditions with an adsorbent comprising an X zeolite molecular sieve exchanged with at least two cations, each selected from Group IIA metals, selectively adsorbing the monoalkyl paraffins and normal paraffins onto the adsorbent and removing the more highly branched paraffins and isopentane from the adsorbent. The adsorbed monoalkyl paraffins and normal paraffins are recovered by desorption with a desorbent selected from the group consisting essentially of isooctane (2,2,4-trimethyl pentane), 2,2,3-trimethyl pentane, 2,3,4-trimethyl pentane, 1,2-dimethyl cyclohexane, 2,2-dimethyl hexane, 2,2-dimethyl octane and 3-ethyl hexane and 2,2,4-trimethyl hexane and may be recycled to an isomerization step. Of the Group IIA metals, mixtures of exchange cations selected from calcium, barium, strontium and magnesium are preferred and a mixture of calcium and strontium are especially preferred. In a preferred adsorbent-desorbent system, much of the higher octane cyclic paraffin content is rejected with the highly branched paraffins. In another preferred embodiment, the desorbent has a higher boiling point than all components of the feed mixture, such as 2,2-dimethyl octane.

DETAILED DESCRIPTION OF THE INVENTION

Figure 1:
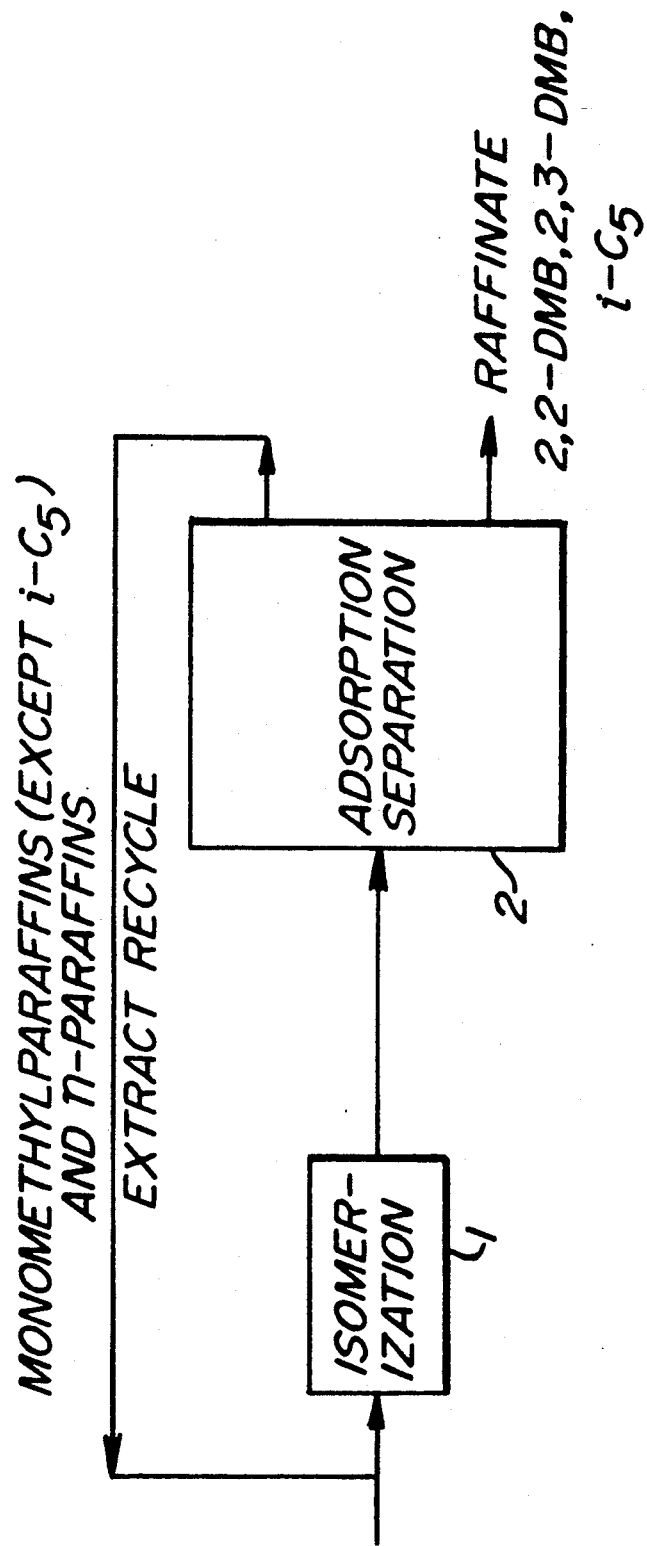
FIG. 1 is a schematic diagram with a flow scheme for a combined isomerization and liquid phase adsorption separation process in accordance with this invention.

A number of specially defined terms are used in describing the preferred simulated moving bed process. The term "feed stream" indicates a stream in the process through which feed material passes to the molecular sieve. A feed material comprises one or more extract components and one or more raffinate components. An "extract component" is a compound or type of compound that is more selectively retained by the molecular sieve while a "raffinate component" is a compound or type of compound that is less selectively retained. In this process, di-branched hydrocarbons and isopentane from the feed stream are raffinate components while normal and other mono-branched hydrocarbons are raffinate components. The term "displacement fluid" or "desorbent" shall mean generally a material capable of displacing an extract component. The term "desorbent input stream" indicates the stream through which desorbent passes to the molecular sieve. The term "raffinate output stream" means a stream through which most of the raffinate components are removed from the molecular sieve. The composition of the raffinate stream can vary from about 100% desorbent to essentially 100% raffinate components. The term "extract stream" or "extract output stream" shall mean a stream through which an extract material which has been displaced by desorbent is removed from the molecular sieve. The composition of the extract stream can also vary from about 100% desorbent to essentially 100% extract components.

The term "selective pore volume" of the molecular sieve is defined as the volume of the molecular sieve which selectively retains extract components from the feedstock. The term "non-selective void volume" of the molecular sieve is the volume of the molecular sieve which does not selectively retain extract components from the feedstock. This volume includes the cavities of the molecular sieve which are capable of retaining raffinate components and the interstitial void spaces between molecular sieve particles. The selective pore volume and the non-selective void volume are generally expressed in volumetric quantities and are of importance in determining the proper flow rates of fluid required to be passed into an operational zone for efficient operations to take place for a given quantity of molecular sieve.

When molecular sieve "passes" into one of the four operational zones (adsorption zone, purification zone, desorption zone, and optional buffer zone), fluid is carried into that zone in both its non-selective void volume and its selective pore volume. The non-selective void volume is utilized in determining the amount of fluid which should pass into the same zone in a countercurrent direction to the molecular sieve to displace the fluid present in the non-selective void volume. If the fluid flow rate passing into a zone is smaller than the non-selective void volume rate of molecular sieve material passing into that zone, there is net entrainment of liquid into the zone by the molecular sieve. Since this net entrainment is a fluid present in a non-selective void volume of the molecular sieve, it, in most instances, comprises less selectively retained feed components.

As is well known from the above-mentioned U.S. Pat. Nos. 2,966,528 and 3,755,144, to increase branched chain hydrocarbons in a paraffin feed, hydrogen and the hydrocarbon feed are contacted in the reaction zone with an isomerization catalyst. The catalyst composites that can be used in the isomerization zone include traditional isomerization catalysts. Such catalysts include high chloride catalyst on an alumina base containing platinum, and crystalline aluminosilicates or crystalline zeolites. Suitable catalyst compositions of this type will exhibit selective and substantial isomerization activity under the operating conditions of the process. Chlorided platinum aluminum catalysts, such as disclosed in the above patents and U.S. Pat. Nos. 3,442,794 and 3,836,597 are preferred because of the significantly lower hydrogen to hydrocarbon ratio made possible in the isomerization zone.

The overall flow scheme for the combined isomerization and separation process is shown in FIG. 1. A $C_5$–$C_6$ feed is introduced into the isomerization reaction zone 1. Effluent from the reaction zone 1 is introduced to the feed inlet of an adsorption column 2 via a rotary valve (not shown) where separation into higher octane and lower octane product streams takes place. The higher octane product stream (raffinate) is removed from the adsorption column 2 via the rotary valve as described elsewhere herein. The extract product stream, containing methyl paraffins (except isopentane) and normal paraffins, is recycled to the isomerization reaction zone 1.

In the isomerization reaction zone 1, the paraffins and monoalkyl paraffins, primarily monomethyl paraffins, in the feed stream are preferably converted to dialkyl, i.e., primarily dimethyl paraffins, which have the highest octane rating. Operating conditions within the isomerization zone, selected to maximize production of di-branched alkanes, include temperatures in the range of 40° to 235° C. and pressures in the range of 7 to 70 bars (g). Lower temperatures within the range are preferred since they favor equilibrium mixtures having higher concentrations of di-branched alkanes. Isomerate is significantly lower in normal paraffin content, i.e., n-C$_5$ and n-C$_6$, and significantly higher in isoparaffins, e.g., isopentane and methyl pentanes, and dimethyl paraffins, e.g., 2,2-dimethyl butane and 2,3-dimethyl butane. Thus, the feed, including recycled extract, may contain about 0-20% (wt.) of dimethyl paraffins, typically from about 5 to 10% (wt.), while the isomerate will contain 6-30% (wt.) dimethyl paraffins.

The effluent from the isomerization reaction zone 1 enters the adsorption zone 2 where it is contacted with an adsorbent. This process is especially suited for adsorption systems that use multiple ports for supplying the process streams to the adsorbent and divide the adsorbent into a plurality of zones for adsorbing paraffins and singly-branched paraffins, removing the relatively non-adsorbed multi-branched paraffi and isopentane, and adsorbing the normal and singly-branched paraffins. A well-known process of this type is the countercurrent moving bed for simulating moving bed countercurrent flow systems. Such systems have a much greater separation efficiency than fixed molecular sieve bed systems. In the moving bed or simulated moving bed processes, the retention and displacement operations are continuously taking place which allows both continuous production of an extract and a raffinate stream and the continuous use of feed and displacement fluid streams. One preferred embodiment of this process utilizes what is known in the art as the simulated moving bed countercurrent flow system. The operating principles and sequence of such flow system are described in U.S. Pat. No. 2,985,589 incorporated herein by reference. In such a system, it is the progressive movement of multiple liquid access points down a molecular sieve chamber that simulates the upward movement of molecular sieve contained in the chamber.

The apparatus which can be utilized to effect the process of this invention may contain a series of individual beds connected by connecting conduits upon which are placed input or output taps to which the various input or output streams can be attached and alternately and periodically shifted to effect continuous operation, e.g., by a rotary valve, such as that described in Broughton U.S. Pat. No. 2,985,589. In some instances, the connecting conduits can be connected to transfer taps which during the normal operations do not function as a conduit through which material passes into or out of the process.

In the typical operation of this process, at least a portion of the raffinate output stream and a portion of the extract output stream will be passed to a separation means wherein at least a portion of the desorbent can be separated to produce a desorbent stream which can be reused in the process and raffinate and extract products containing a reduced concentration of desorbent. The separation means will typically be a fractionation column, the design and operation of which is well known to the separation art.

Reference can be made to said Broughton U.S. Pat. No. 2,985,589, and to a paper entitled "Continuous Adsorptive Processing—A New Separation Technique" by D. B. Broughton presented at the 34th Annual Meeting of the Society of Chemical Engineers at Tokyo, Japan on Apr. 2, 1969, both references incorporated herein by reference, for further explanation of the simulated moving bed countercurrent process flow scheme.

Although both liquid and vapor phase operations can be used in many adsorptive type separation processes, liquid-phase operation is preferred for this process because of the lower temperature requirements and because of the higher yields of raffinate product that can be obtained with liquid-phase operation over those obtained with vapor-phase operation. Adsorption conditions will, therefore, include a pressure sufficient to maintain liquid phase. Adsorption conditions will include a temperature range of from about 60° C. to about 200° C., with about 100° C. to about 120° C. being preferred and a pressure sufficient to maintain liquid-phase, ranging from about atmospheric to about 500 psig with from about atmospheric to about 200 psig usually being adequate. Desorption conditions will include the same range of temperatures and pressures as used for adsorption conditions.

The feed to the separation zone is the effluent of the isomerization zone from which hydrogen gas is removed and recycled to the isomerization reaction and from which any light materials may be removed. Feed components and concentration may be in the ranges set forth in the following Table 1 along with a typical feed composition. The Research Octane Numbers (RON) (Clear) of the components of the feed are also listed.

TABLE 1

| Component | Research Octane No. (RON) (Clear) | Typical Composition (wt. %) | Range (wt. %) |
|---|---|---|---|
| propane | — | 0.1 | 0-0.2 |
| i-butane | 100+ | 0.9 | 0-5 |
| n-butane | 93.6 | 0.1 | 0-5 |
| i-pentane | 92.3 | 28.1 | 20-50 |
| n-pentane | 61.7 | 8.6 | 5-20 |
| cyclopentane | 100.0 | 1.6 | 0-3 |
| 2,2-dimethyl butane | 91.8 | 14.9 | 5-25 |
| 2,3-dimethyl butane | 101.7 | 4.8 | 2-10 |
| 2-methyl pentane | 73.4 | 13.7 | 10-20 |
| 3-methyl pentane | 74.5 | 7.8 | 5-15 |
| n-hexane | 24.8 | 5.2 | 2-10 |
| methyl cyclopentane | 92.1 | 5.4 | 0-10 |
| cyclohexane | 83.0 | 7.2 | 0-10 |
| C$_7$+ | 100+ | 1.7 | 0-5 |
| | | 100.1 | |

The adsorbent used in the invention has the capability of selectively rejecting the di-branched paraffins and the isopentane and adsorbing the normal and mono-branched paraffins. Prior processes, such as taught in the above-mentioned patents, U.S. Pat. Nos. 4,717,784 and 4,855,529, have rejected di-branched paraffins and adsorbed normal and mono-branched paraffins, but isopentane was adsorbed along with lower octane components, making it necessary to add separate steps to recover the octane values of the isopentane in the feed. The adsorbents of the invention, capable of selectively rejecting the high octane components of the feed. including isopentane. are highly advantageous since the recovery of octane values of an isomerate stream is simplified and recovery costs are lower. In addition. when the higher octane components are in greater volume in the isomerate. a more efficient process may result since the non-adsorbed components pass directly through the adsorbent while the components in lower volume are adsorbed and desorbed during each cycle. thereby increasing the volume throughput of feed to the separation. The adsorbents capable of selectively adsorbing both monomethyl paraffins and normal paraffins and rejecting the di-branched paraffins and isopentane are X zeolites exchanged with at least two Group IIA cations. preferably selected from the group consisting of calcium. barium. strontium and magnesium. The most preferred combination is calcium/strontium. (CaSrX) because the cyclic hydrocarbons can be rejected to the raffinate with the high octane components. Others that have been found useful are BaSrX; CaMgX and MgSrX. but the cyclic hydrocarbon components are coextracted with the lower octane components. In the preferred combinations of cations. the strontium level is between 2 and 16 wt. %. based on total adsorbent. including binder. and preferably from 2% to 10%. Calcium. barium and magnesium vary from 2% to 14%. preferably from 2-5 wt. %.

Typically. adsorbents used in separation processes. such as described herein. contain the crystalline material dispersed in an amorphous inorganic matrix or binder. having channels and cavities therein which enable liquid access to the crystalline material. Amorphous material such as silica. or silica-alumina mixtures or compounds. such as clays. are typical of such inorganic matrix materials. The preferred binder for the separation of this invention is bentonite. The binder. typically in amounts ranging from 2-25% by weight. aids in forming or agglomerating the crystalline particles of the zeolite which otherwise would comprise a fine powder. The adsorbent may thus be in the form of particles such as extrudates. aggregates. tablets. macrospheres or granules having a desired particle size range. from about 16 to 40 mesh (Standard U.S. Mesh) (1.9 mm to 230 $\mu$m).

In the separation of the present invention. it is preferred that the level of water content of the adsorbent be maintained at or below about 4.5% (LOI). and preferably between about 1% and 3% (LOI). The faujasites selectively adsorb normal paraffins and monomethyl paraffins, but, at low water content. exhibit a reversal of selectivity at about 4.7% (LOI). At water levels below about 2.0% (LOI). cyclohexane is rejected with the high octane components with CaSrX adsorbent, and therefore a most preferred range of water is from about 1% to about 2% (LOI).

In this process, and, particularly, the preferred continuous, simulated moving bed process, the desorbent must be selected to satisfy the following criteria: First, the desorbent material should displace an extract component from the adsorbent with reasonable mass flow rates without itself being so strongly adsorbed in the following adsorption cycle. Secondly, the desorbent material must be compatible with the particular adsorbent and the particular feed mixture: it must not reduce or destroy the critical selectivity of the adsorbent for an extract component with respect to a raffinate component and must be easily separable from the feed mixture that is passed into the process. Further, it will preferably have a substantially different average boiling point than that of the feed mixture. i.e.. more than about 5° C. difference. to allow separation of at least a portion of desorbent material from feed components in the extract and raffinate streams by simple fractional distillation. thereby permitting reuse of desorbent material in the process and should also be readily available and reasonable in cost. However, a suitable desorbent or desorbents for a particular separation with a specific adsorbent are not always predictable. In the preferred isothermal, isobaric, liquid-phase operation of the process of our invention. certain singly-branched or multi-branched lower alkyl-substituted paraffins meet the criteria as the desorbent material. Isooctane is a preferred desorbent, in that it is relatively easily available and inexpensive. However, if the feed contains heavy components which have a higher boiling point than isooctane (2,2,4-trimethyl pentane-b.p. = 99.2° C.) additional fractionating equipment is required to remove them from the feed prior to the adsorptive separation. In this case, other "heavier" desorbents are preferable. Such preferred higher boiling (heavy) desorbents have a boiling point higher than about 105° C. and include 2,3,4-trimethyl pentane. 2,2,3-trimethyl pentane, 3-ethyl hexane. 2,2-dimethyl hexane, and 1,2-dimethyl cyclohexane and 2,2-dimethyl octane.

A dynamic testing apparatus is employed to test various adsorbents with a particular feed mixture and desorbent material to measure the adsorption characteristics of retention. capacity and exchange rate. The apparatus used herein consisted of a helical adsorbent chamber of approximately either 70 cc or 14 cc volume having inlet and outlet portions at opposite ends of the chamber. The chamber is contained within a temperature control means and. in addition, pressure control equipment is used to operate the chamber at a constant predetermined pressure. Quantitative and qualitative analytical equipment such as refractometers. polarimeters and chromatographs can be attached to the outlet line of the chamber and used to detect qualitatively. or determine quantitatively. one or more components in the effluent stream leaving the adsorbent chamber. A pulse test. performed using this apparatus and the following general procedure, is used to determine data. e.g.. selectivity. for various adsorbent systems. The adsorbent is placed in a chamber and filled to equilibrium with a particular desorbent material by passing the desorbent material through the adsorbent chamber. At a convenient time. a pulse of feed containing known concentrations of a tracer and of a particular extract component or of a raffinate component or both, all diluted in desorbent material is injected for a duration of several minutes. Desorbent material flow is resumed, and the tracer and the extract component or the raffinate component (or both) are eluted as in a liquid-solid chromatographic operation. The effluent can be analyzed on-stream or alternatively, effluent samples can be collected periodically and later analyzed separately by analytical equipment and traces of the envelopes or corresponding component peaks developed.

From information derived from the test, adsorbent performance can be rated in terms of void volume, net retention volume (NRV) for an extract or a raffinate component, the rate of desorption of an extract component from the adsorbent and selectivity. The net retention volume of an extract or a raffinate component may be characterized by the distance between the center of the peak envelope of the extract or raffinate component and the center of the peak envelope of the tracer component (void volume) or some other known reference point. Gross retention volume (GRV) is the distance between the center of a peak envelope and the zero abscissa and measured as total ml. of desorbent material pumped during this interval. NRV is also the difference between the respective GRVs and the GRV of the tracer. It is expressed in terms of the volume in cubic centimeters of desorbent material pumped during this time interval represented by the distance between the peak envelopes. The rate of exchange or desorption rate of an extract component with the desorbent material can generally be characterized by the width of the peak envelopes at half intensity. The narrower the peak width, the faster the desorption rate. Selectivity, $\beta$, is determined by the ratio of the net retention volumes of the more strongly adsorbed component to each of the other components.

The examples shown below are intended to further illustrate the process of this invention without unduly limiting the scope and spirit of said process. The examples present test results for various adsorbent and desorbent materials when using the above dynamic testing apparatus.

EXAMPLE I

In this experiment, five pulse tests, as described above, were performed to evaluate an X zeolite exchanged with a mixture of calcium and strontium cations at various levels in separating high octane components from an isomerization reaction product stream. The desorbent in each test was isooctane (2,2,4-trimethyl pentane). The level of water, determined by percent loss on ignition (LOI), and strontium level, as percent (wt.) of total adsorbent (including binder) are indicated in the following Table 2, as well as the cyclics, e.g., cyclohexane (CH) and/or methyl cyclopentane (MeCP) which are rejected to the raffinate with the other high octane components and the critical selectivity ($\beta$) of those components with respect to 3-methyl pentane (3-MP), the least strongly adsorbed low octane component. Net retention volumes (NRV) for isopentane and 3-methyl pentane are also given in Table 2 to illustrate the degree of selectivity of the adsorbent for these two components. As indicated in the table, isopentane, a desirable high octane component, is rejected with the raffinate, as shown by the selectivity ($\beta$) with respect to 3-MP, of 1.6-1.8. The operating temperature of the column in each of the experiments was 100° C. except in pulse test No. 4, which was 120° C.

TABLE 2

| Pulse Test No. | Strontium Level | LOI at 900° C. | Cyclics in Raffinate Selectivity ($\beta$) | NRV i-C$_5$ | NRV 3 MP | $\beta$ 3MP/i-C$_5$ |
|---|---|---|---|---|---|---|
| 1 | 2.57 | 2.63 | CH:$\beta$ = 1.17 | 5.1 | 8.1 | 1.6 |
| 2 | 2.22 | 3.5 | CH:$\beta$ = 1.14 | 3.9 | 7.0 | 1.8 |
| 3 | 8.25 | 3.22 | MeCp:$\beta$ = 1.23 | 4.3 | 7.5 | 1.7 |
|   |      |      | CH:$\beta$ = 1.32 |     |     |     |
| 4 | 8.25 | 3.22 | MeCP:$\beta$ = 1.14 | 4.3 | 7.4 | 1.7 |
|   |      |      | CH:$\beta$ = 1.28 |     |     |     |
| 5 | 16.8 | 2.39 | MeCP:$\beta$ = 1.13 | 6.4 | 10.2 | 1.6 |
|   |      |      | CH:$\beta$ = 1.14 |     |     |     |

Calcium levels (wt. %) in Pulse Tests 1-5 were 2.86; 4.68; 4.0; 4.0 and 2.39, respectively. The balance of ions in each case was sodium; for example, Pulse Test No. 1, which had low strontium and low calcium content, contained 4.63% sodium.

From the data above, the best separation of cyclics (methyl cyclopentane and cyclohexane) from the low octane components is achieved at a strontium level of 8.25% (wt.). The temperature does not appear to be a significant factor.

Figure 2:
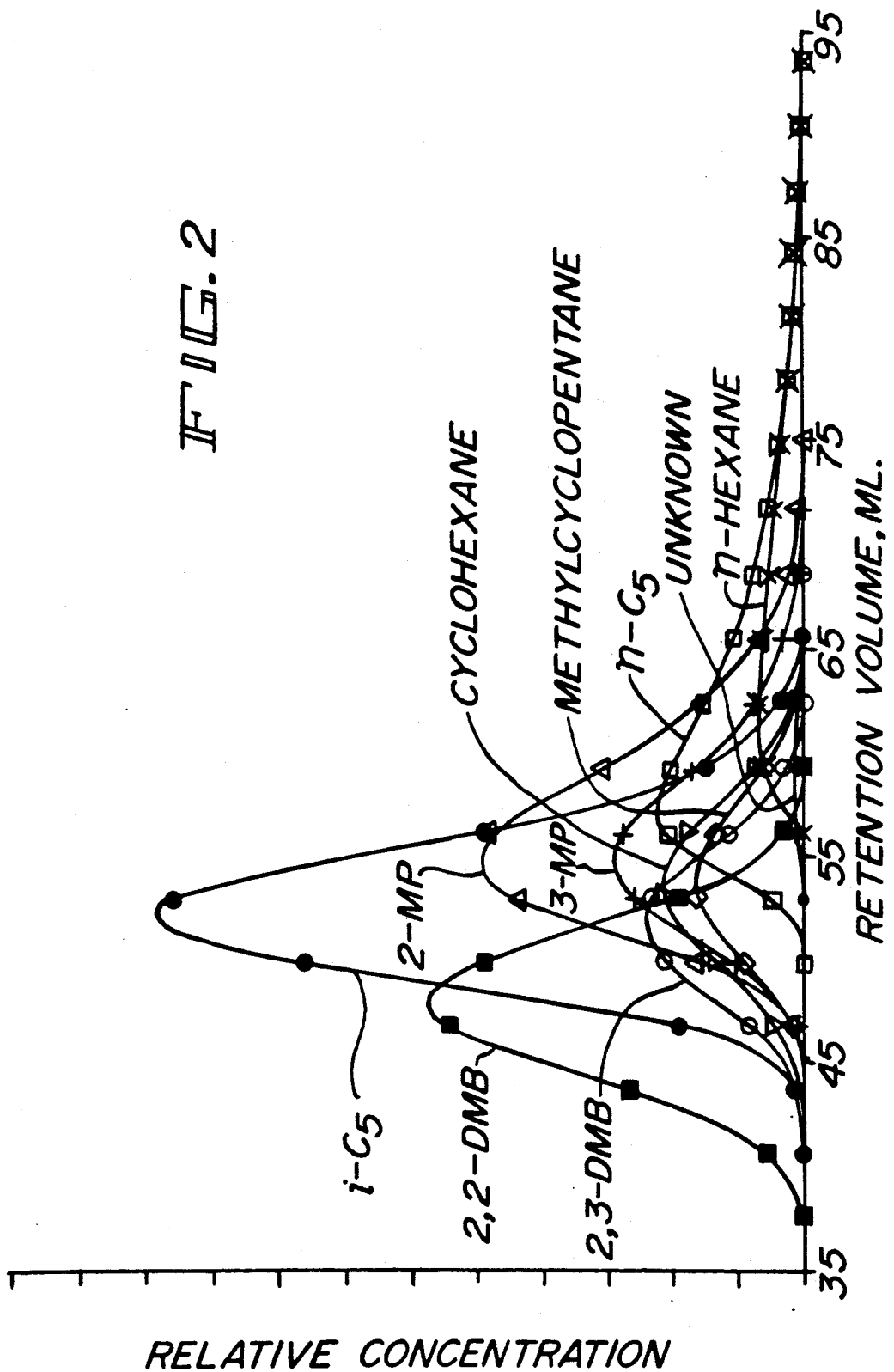
FIG. 2 is a graphic representation of the results of a chromatographic pulse test separation of isomerate into higher and lower octane products with X zeolite exchanged with calcium and strontium and desorbed with isooctane.

The pulse test results for Test No. 3 is shown in FIG. 2 and the data are given below in Table 3 under column headings gross retention volume (GRV), net retention volume (NRV) and selectivity ($\beta$).

TABLE 3

| Component | GRV | NRV | Selectivity ($\beta$) |
|---|---|---|---|
| 2,2-dimethyl butane (2,2-DMB) | 48.0 | 0.0 | ∞ |
| 2,3-dimethyl butane (2,3-DMB) | 51.9 | 3.9 | 1.91 |
| isopentane | 52.3 | 4.3 | 1.73 |
| cyclohexane (CH) | 53.7 | 5.7 | 1.32 |
| methyl cyclopentane (MeCP) | 54.1 | 6.1 | 1.23 |
| 3-methyl pentane (3-MP) | 55.5 | 7.5 | 1.00 |
| 2-methyl pentane (2-MP) | 55.8 | 7.8 | 0.96 |
| n-pentane | 60.1 | 12.1 | 0.62 |
| Unknown | 60.1 | 12.1 | 0.62 |
| hexane | 66.4 | 18.4 | 0.41 |

COMPARATIVE EXAMPLE 1

A pulse test was run to illustrate the superiority of the presently disclosed mixed cation X zeolite over the potassium-barium X zeolites disclosed by Neuzil et al U.S. Pat. No. 3,706,813 for separating multibranched paraffins from singly-branched and normal paraffins. The desorbent was isooctane and all other conditions were essentially similar to Example I.

A feed having the same composition as Example I was injected into the pulse test column containing 70 cc of barium-potassium exchanged zeolite at 100° C. The results are given in the following Table 4, under column headings, gross retention volume (GRV), net retention volume (NRV) and selectivity ($\beta$) with respect to 3-methyl pentane (3-MP).

TABLE 4

| Component | GRV | NRV | Selectivity ($\beta$) |
|---|---|---|---|
| 2,2-dimethyl butane | 47.6 | 0.0 | ∞ |
| 2,3-dimethyl butane | 48.9 | 1.3 | 2.50 |
| 3-methyl pentane | 50.6 | 3.0 | 1.00 |
| isopentane | 51.0 | 3.3 | 0.91 |
| 2-methyl pentane | 54.8 | 7.2 | 0.42 |
| isobutane | 55.6 | 8.0 | 0.38 |
| n-pentane | 56.8 | 9.2 | 0.33 |
| methyl cyclopentane | 57.7 | 10.0 | 0.30 |
| cyclohexane | 78.7 | 30.7 | 0.10 |
| n-hexane | 90.8 | 43.1 | 0.07 |

As seen from the same data, isopentane, a high octane component, cannot be separated from 3-MP and the other lower octane components of the feed blend, thus losing the octane value of that component for the raffinate product stream and requiring additional processing steps to recover the octane value.

EXAMPLE II

Example I was repeated except the exchanged mixed cations were other combinations of Group II-A metals, calcium-magnesium, calcium-barium, barium-strontium and magnesium-strontium. The desorbent was isooctane. The column operating temperature in each was 100° C., except Test No. 7, in which the temperature was 130° C. The results of these tests are given in the following Table 5.

TABLE 5

| Pulse Test No. | Metal Level (wt. %) | % LOI (at 900° C.) | Cycles in Raffinate Selectivity (β) | β3 mP/i-C5 |
|---|---|---|---|---|
| 6 | 2.6% Mg 4.15% Ca | 2.6 | MeCP:β = 1.1 CH:β = 1.2 | 1.2 |
| 7 | 17.3% Ba 4.36% Ca | 1.21 | none | 1.3 |
| 8 | 9.06% Sr 13.77% Ba | 2.56 | none | 1.2 |
| 9 | 2.8% Mg 12.9% Sr | 2.56 | none | 1.4 |

As seen from the critical selectivity (3 MP/i-C5), all are able to reject isopentane with the dimethyl paraffins and adsorb 3-methyl pentane. However, most of the cyclics are separated with the extract with these mixtures of Group IIA metal exchange ions.

EXAMPLE III

Figure 3:
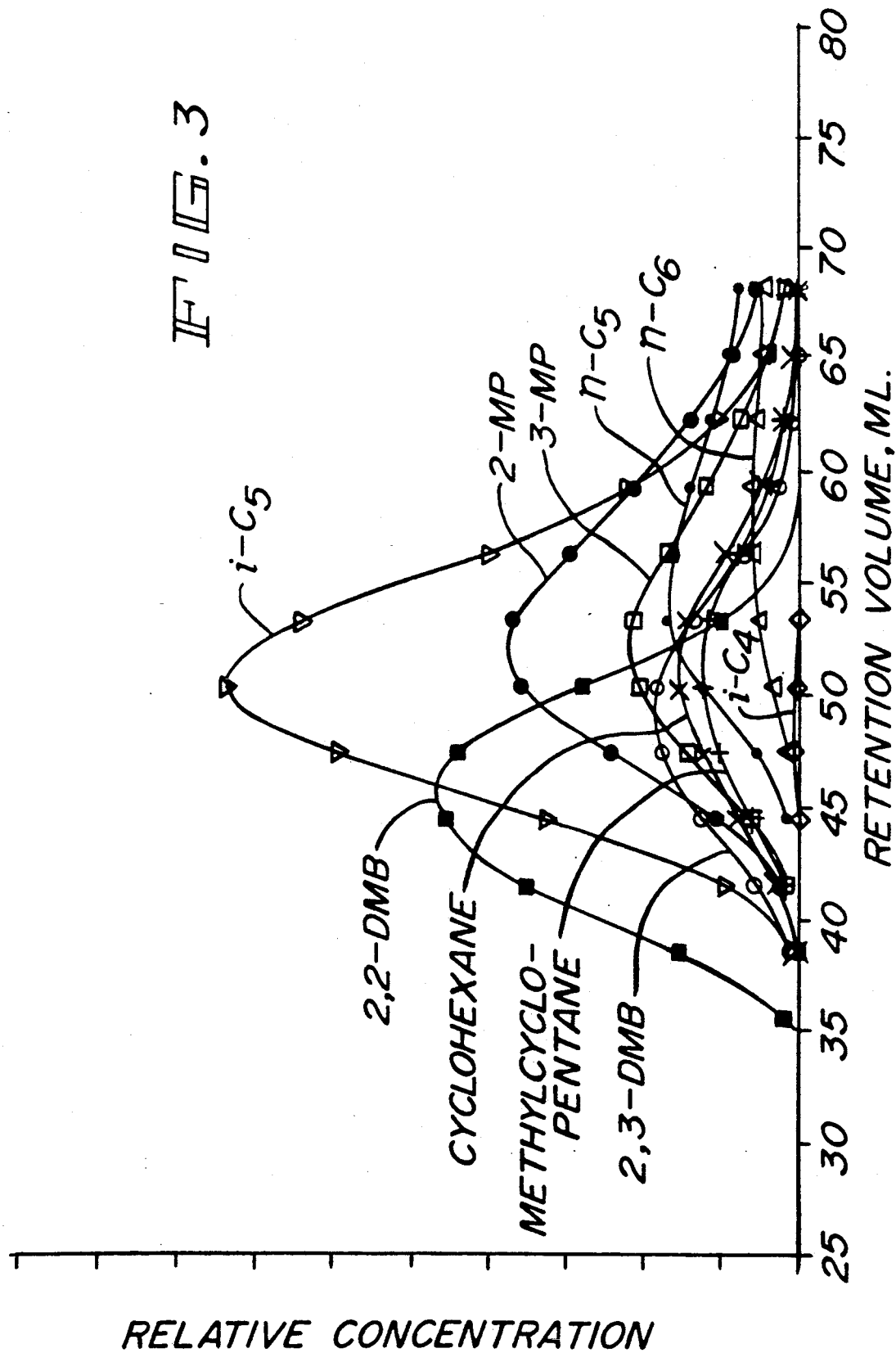
FIG. 3 is similar to FIG. 2 except that the desorbent was 1,2-dimethyl cyclohexane.

Example I was repeated with the same adsorbent at 2.22% (wt.) strontium level and 4.68% calcium, but the desorbent was cis-1,2-dimethyl-cyclohexane instead of isooctane. Another sample of the same feed was used. The column temperature was 100° C. The results of the separation are set forth in FIG. 3 in the following Table 6.

TABLE 6

| Component | GRV | NRV | Selectivity (β) |
|---|---|---|---|
| 2,2-dimethyl butane | 45.4 | 0.0 | ∞ |
| iso-butane | 48.8 | 3.5 | 2.2 |
| 2,3-dimethyl butane | 49.1 | 3.7 | 2.1 |
| cyclohexane | 50.8 | 5.4 | 1.4 |
| isopentane | 50.8 | 5.4 | 1.4 |
| methyl cyclopentane | 51.0 | 5.7 | 1.3 |
| 3-methyl pentane | 53.0 | 7.6 | 1.00(Ref) |
| 2-methyl pentane | 53.3 | 7.9 | 0.96 |
| n-hexane | 57.4 | 12.0 | 0.63 |
| n-pentane | 57.4 | 12.0 | 0.63 |

With this preferred combination of absorbent and desorbent, the valuable cyclic high octane components, can be separated with the multibranched paraffin and isopentane and sent directly to the gasoline pool.

EXAMPLE IV

A further series of light (low boiling) and heavy (high boiling) desorbents was screened with a so-called reverse pulse tests in which the selected adsorbent is contacted with a mixture of the heavy desorbents and desorbed with a feed component. In this case, the desorbent was selected to have a structure similar to the multibranched paraffins of the raffinate; the desorbent was 2,2,4-trimethyl pentane (isooctane) (b.p.=99.2° C.). A balanced desorbent for the separation to be determined by these pulse tests will have a lower retention volume than the least strongly adsorbed extract component, 2-methyl pentane, and preferably have a retention volume close to the void volume (approx. 45 ml.) and a reasonably high transfer rate as measured by the width of the peak at one-half the peak height. Half widths below about 9 ml. were assumed to be acceptably good rates. The gross retention volume (GRV) of 2-methyl pentane was 58.0 ml. Suitable heavy desorbents are listed in Part A of Table 7 and, for comparison, some materials which were tested, but deemed not acceptable for use as desorbents in the separation of the invention are listed in Part B. Included in Part B are materials which boil in the same range as the feed and, although they are effective desorbents (GRV in the range 51–57), are not suitable for the separation since they are not easily separated from the raffinate or extract output streams by simple fractionation.

TABLE 7

| Compound | Boiling Point (°C.) | GRV (ml) | Width at ½ height (ml) |
|---|---|---|---|
| Part A | | | |
| 2,2-dimethyl hexane | 106.8 | 51.6 | 7.87 |
| 2,2,3-trimethyl pentane | 109.8 | 54.2 | 7.93 |
| 2,3,4-trimethyl pentane | 113.5 | 55.4 | 8.76 |
| 3-ethyl hexane | 118.5 | 52.3 | 7.88 |
| 2,3,4-trimethyl hexane | 126.6 | 57.6 | 8.50 |
| 2,2-dimethyl octane | 156.9 | 52.5 | 7.88 |
| Part B | | | |
| 2,4-dimethyl pentane | 80.5 | 53.0 | 7.52 |
| 2,2,3-trimethyl butane | 80.9 | 51.4 | 8.18 |
| 2,3-dimethyl pentane | 89.8 | 55.7 | 8.28 |
| 2-methyl hexane | 90.0 | 60.0 | 10.65 |
| 2,5-dimethyl hexane | 109.0 | 60.7 | 11.76 |
| 2-methyl heptane | 117.6 | 62.5 | 13.58 |
| propyl cyclopentane | 130.95 | 65.7 | 15.00 |
| n-decane | 174.00 | 61.7 | 10.64 |
| 3,3,5-trimethyl heptane | 155.7 | 65.1 | 14.67 |
| 3,6-dimethyl octane | 160.8 | 57.5 | 11.27 |
| 2,2,4,4,6,8,8-heptamethyl-nonane | 240 | 60.4 | 11.27 |
| 2,6,10,14-tetramethyl-pentadecane | 166 | 77.5 | 30.8 |

What is claimed is:

1. A continuous process for separating higher octane components comprising dimethyl paraffins (DMP's) and iso-paraffins from a $C_5$ and $C_6$ feed mixture containing DMP's, monomethyl paraffins, including isopentane, and normal paraffins comprising contacting at adsorption conditions said feed mixture with an adsorbent comprising an X zeolite molecular sieve exchanged with at least two cations, each selected from Group IIA metals, at the exchangeable sites to selectively adsorb said monoalkyl paraffins, except isopentane, and normal paraffins, removing said DMP's and isopentane from said adsorbent and desorbing the adsorbed monoalkyl paraffins and normal paraffins.

2. The process of claim 1 wherein said adsorbed paraffins are desorbed with a desorbent selected from the group consisting essentially of isooctane (2,2,4-trimethyl pentane) 2,2,3-trimethyl pentane, 2,3,4-trimethyl pentane, cis-1,2-dimethyl cyclohexane, 2,2-dimethyl hexane, 2,2-dimethyl octane, 3-ethyl hexane, 2,2,4-trimethyl hexane and mixtures thereof.

3. The process of claim 1 wherein said exchange cations are selected from the group consisting of calcium, barium, strontium and magnesium.

4. The process of claim 3 wherein said exchange cations are calcium and strontium.

5. The process of claim 3 wherein said exchange cations are barium and calcium.

6. The process of claim 1 wherein said feed additionally contains cyclic paraffins which are relatively non-adsorbed and are removed with said non-adsorbed DMP's and isopentane.

7. The process of claim 6 wherein said desorbent is cis-1,2-dimethyl cyclohexane.

8. The process of claim 1 wherein said desorbent is 2,2-dimethyl octane.

9. The process of claim 1 wherein the water level of said adsorbent is about 4.5%, as determined by loss on ignition (LOI at 900° C.) or less.

10. The process of claim 1 wherein the water level is from about 1% to about 2%, as determined by loss on ignition (LOI at 900° C.).

11. The process of claim 1 wherein one of said exchange cations is strontium.

12. The process of claim 10 wherein said strontium ions constitute from 2% to 10% (wt.) of said adsorbent.

* * * * *